(12) United States Patent
Kim

(10) Patent No.: US 7,662,853 B2
(45) Date of Patent: Feb. 16, 2010

(54) MONOACETYLDIACYLGLYCEROL DERIVATIVE FOR THE TREATMENT OF SEPSIS

(76) Inventor: Sang-Hee Kim, Sinhyundaivilla 1-302, 42, Garakbon-Dong Song Pa-Gu, Seoul 138-169 (KR)

( * ) Notice: Subject to any disclaimer, the term of this patent is extended or adjusted under 35 U.S.C. 154(b) by 86 days.

(21) Appl. No.: 11/587,377

(22) PCT Filed: Apr. 22, 2005

(86) PCT No.: PCT/KR2005/001175
§ 371 (c)(1),
(2), (4) Date: Jul. 31, 2007

(87) PCT Pub. No.: WO2005/112912
PCT Pub. Date: Dec. 1, 2005

(65) Prior Publication Data
US 2008/0200543 A1 Aug. 21, 2008

(30) Foreign Application Priority Data
Apr. 24, 2004 (KR) .................. 10-2004-0028514
Sep. 4, 2004 (KR) .................. 10-2004-0070650
Dec. 21, 2004 (KR) .................. 10-2004-0109805

(51) Int. Cl.
*A61K 31/22* (2006.01)
*A61P 35/00* (2006.01)
*A61P 37/00* (2006.01)

(52) U.S. Cl. .................. 514/547; 514/546; 514/560

(58) Field of Classification Search .................. None
See application file for complete search history.

(56) References Cited

U.S. PATENT DOCUMENTS
2003/0032674 A1* 2/2003 Hwang .................. 514/560

FOREIGN PATENT DOCUMENTS
KR 10-2005-0103259 10/2005

WO WO 99/26640 A1 6/1999
WO WO 03/063793 * 8/2003

OTHER PUBLICATIONS

Lambert, Eur J Pharam Sci, 11 (suppl 2): S15-S27, 2000.*
PDF Merck Manual regarding "Sepsis".*
Suh, Jeong S., et al., Triacylglycerol, 1-Palmitoyl-2-Linoleoyl-3-Acetyl-rac-Glycerol Isolated from Bovine Udder . . . , Cellular Physiology and Biochem., 13: 415-422 (2003).
Suh, Jeong-Sook, et al., Phagocytic Activity of Ethyl Alcohol Fraction of Deer Antler in Murine Peritoneal Macrophage, Biol. Pharm., Bull., 22: 932-935 (1999).
Kim, MiJung, et al., The Effects of GM-CSF, SCF and Deer Antler Extracts on the Mouse Hematopoietic Cells, Korea J. BRM, 4(1): 47-53 (1994).
Kim, Sang Hee, et al., Biological Effects of Deer Antler Extracts on Hematopoietic System, Korean J. BRM, 3(1): 23-30 (1993).
Ouyang, Yanli, et al., Suppression of Interleukin-2 by the Putative Endogenous Cannabinoid 2-Arachidonyl-Glycerol . . . , Molecular Pharm., 53: 676-683 (1998).

* cited by examiner

*Primary Examiner*—Brian-Yong S Kwon
*Assistant Examiner*—Bong-Sook Baek
(74) *Attorney, Agent, or Firm*—Elmore Patent Law Group, P.C.; Carolyn S. Elmore; Roy P. Issac

(57) ABSTRACT

The uses of mono acetyl diacyl glycerol derivatives extracted from deer antler for immunomodulating agent disclosed. Medical supplies and health foods containing the same as an effective ingredient also disclosed. Mono acetyl diacyl glycerol derivatives shows significantly effect for immuno modulation including immune enhancing. In the case of inducing cancer in a hamster by injecting cancer cell line, cancer development was delayed by activating lymphocytes, monocytes, and dendritic cells that are important factors to promote immunity and apoptosis of cancer cell was induced by promoting cytotoxicity of immune cell against cancer cell. Also in the case of mouse induced septic shock, it shows 100% survival rate even after lapse of 120 hours by control of immune function and suppression effect apoptosis. Therefore, mono acetyl diacyl glycerol derivatives according to the present invention can be effectively used for an immunomodulating agent, a sepsis treatment, a cancer treatment, and a health food for an immune modulation or the prevention of cancer.

3 Claims, 6 Drawing Sheets

MONOACETYLDIACYLGLYCEROL DERIVATIVE FOR THE TREATMENT OF SEPSIS

BACKGROUND ART

This invention relates to uses of immunomodulating agent, medical supplies, and health foods containing mono acetyl diacyl glycerol derivatives extracted from deer antler as an effective ingredient.

Antler (in Latin, Cervi parvum cornu) is an uncalcified horn harvested and dried from any animal of the deer family. In traditional oriental medicine in Korea, deer antlers together with ginseng have been widely used for their various acclaimed medicinal effects. The deer family for the traditional use of antlers are limited only *Cervus nippon* Temminick var. *mantchuricus Swinhoe*(Referred as C.N. hereafter) and *Cervus elaphus* L. Deer antler has been acclaimed to have numerous medicinal effects. It has been known to be efficacious in tonic agents, growth and development promotion, hematopoiesis, treating nervous breakdown, treating cardiac insufficiency, and generally improving the function of the five viscera and six entrails (Dong-euibogam, a classical medical literature in Korea). Other literatures in traditional medicine, concerning the effects of deer antlers, also reported that tonic effects, nourishing effect, strengthening vitality effects including improving cardiac function, relieving fatigue effects, enhancing immunity. Many attempts have been made to uncover the curious chemical make-up of antler. As a result, it is found to contain active gradients such as free amino acids, trace (metallic) elements, hexose, pentose, hexosamine, uronic acid, sialic acid, mucopolysaccharides (e.g. hyaluronic acid, chondroitin A), various fatty acids, prostaglandins. It has also been reported that glycolipid, phospholipid, cholesterol, hypoxanthine, cholest-5-ene-3$\beta$,7$\alpha$-diol, cholesterol ester, polyamine were detected in the extracts from deer antler. Others reported the presence of estrone, and estradiol receptor (report of NIH Korea, Vol. 22, p 359, 1985; Korean Biochem. J, Vol. 9, No. 3, p 153, 1976; Korean Biochem. J, Vol. 9, No. 4; p 215, 1976; Korean Biochem. J, Vol. 10, No. 1, p 1, 1977; Shoykugaku Zasshi, 43(2), p 173, 1989).

Immunity is a defense mechanism protecting a living body from various pathogens. Immunodeficiency is resulted from a defect in a constituent of immune system, indicating that immune system is unable to response to various antigens. Immunodeficiency is largely divided into congenital or primary immunodeficiency and acquired or secondary immunodeficiency. In the case of congenital immunodeficiency, B-cells or T-cells do not exist naturally, so it can be treated only by gene therapy, antibody insertion and bone marrow transplantation. On the other hand, in the case of acquired immunodeficiency, all the immune related factors exist naturally but there is malfunctioning in immune response, so it can be improved by promoting the functions of immune factors. Recently the outbreak of autoimmune diseases such as arthritis, atopy, dementia and sepsis have been increased. Autoimmune diseases are resulted from over increasing of immune function. An immune suppressor has been used to remedy autoimmune diseases, but the immune suppressor also causes decreasing of immunity frequently. Based on the disclosure of immune mechanism, various attempts have been made to develop an immune regulator for the control of immunity. The purpose of these attempts is for increasing defensive power of a living body against pathogens and minimizing side-effects by controlling promotion or suppression of immune function with immune regulators which can stimulate immune cells non-specifically. Immune regulators can remedy almost diseases of living body such as cancer, sepsis, degenerative arthritis, infection, dementia, aging, diabetes, anemia, skin disease, asthma, atopy, stress, nerve breakdown, physical fatigue, chronic fatigue syndrome, and osteoporosis. As of today, chemical compounds, microorganism compositions, biological products, etc, have been used as an immune regulator. Most of those immune regulators are limited in using because they are inclined to work only one effect (either immune promotion or suppression). Therefore, they may cause side effects and have toxicity themselves. In order to overcome above mentioned problems, foodstuffs without toxicity, effective ingredients extracted from natural sources and the traditional herb medicines are the major targets to develop immune regulators and experiments to examine their effects as a medicine have been on trial. But these immune regulators still have either immune promotion or suppression effect.

Cancer, the leading cause of death in Korea, has been increasing every year. Chemo-therapy or radio-therapy for the treatment of cancer not only kills cancer cells but also destroys normal bone marrow cells, especially hematopoietic cells regulating immunity and hematopoieses, resulting in the malfunction of immune system and hematopoietic organ (Korean J. BRM., 1, p 23, 1993; Korean J. BRM., 4, p 47, 1994; Crit. Rev Oncol Hematol. 1, p 227, 1984). Sepsis is a serious disease having over 45% lethal rate caused by a severe systemic infection leading to a systemic inflammatory response. It almost happens when infected hosts response excessively against endotoxin from gram negative bacteria. However Antibiotics, steroid, or Xigris (Eli Lilly company) have been used as a septic shock treatment, the lethal rate from septic shock is still high because theses antibiotics, steroid, or Xigris are ineffective against sepsis.

Thus, the present inventors separated various ingredients of C.N. antler which has been known to having excellent pharmaceutical effects as a folk remedy, and further observed that one of those effective ingredients of C.N. antler, mono acetyl diacyl glycerol, showed significant immune regulation activity in vivo. As a result of immune regulation effects, the C.N. antler has a possibility of using for septic shock treatment and anti-cancer agent without causing toxicity in vivo. And, the present inventors completed this invention by confirming that mono acetyl diacyl glycerol of the invention can be used as a safe immune enhancing agent, an immunomodulating agent, a septic shock treatment and an anti-cancer agent.

DISCLOSURE

Technical Problem

Therefore, it is an object of the present invention to provide an immunomodulating agent, a septic shock treatment, an anti-cancer agent, and health foods containing mono acetyl diacyl glycerol derivatives as an effective ingredient. Health foods are for modulating immune, preventing or treating septic shock and cancer.

Technical Solution

In order to achieve the above object, the present invention provides an immunomodulating agent containing mono acetyl diacyl glycerol derivatives represented by the following formula 1 as an effective ingredient.

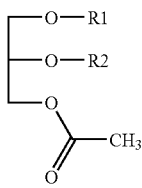

[Formula 1]

wherein, R1/R2 is 9-octadecenoyl(oleoyl)/hexadecanoyl (palmitoyl), hexadecanoyl (palmitoyl)/(9-octadecenoyl(oleoyl), hexadecanoyl(palmitoyl)/9,12-octadecadienoyl(linoleoyl), hexadecanoyl(palmitoyl)/9,12,15-octadecatrienoyl (linolenoyl) or hexadecanoyl(palmitoyl)/5,8,11,14-eicosatetraenoyl(arachidonoyl).

Here, above mentioned mono acetyl diacyl glycerol derivatives represented by the below formula 2 is preferred.

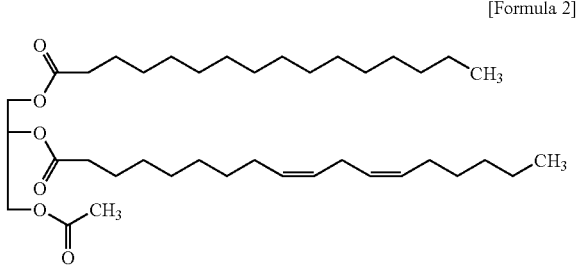

[Formula 2]

The present invention also provides an AIDS treatment, a sepsis treatment, and an anti-cancer agent containing mono acetyl diacyl glycerol derivatives of formula 1 as an effective ingredient. The present invention further provides health foods containing mono acetyl diacyl glycerol derivatives of formula 1 as an effective ingredient for an immune modulation or the prevention of cancer.

A: a microscopic photograph taken right after the inoculation of mouse bone marrow cells with the density of $1 \times 10^6$ cells/ml ($\times 100$).

B: a microscopic photograph showing the round bone marrow stem cells after three days culture. Those cells formed a cluster, which was growing on the bottom of a well of a cell culture plate ($\times 400$).

C: a microscopic photograph of the growing mature dendritic cells which are forming cluster on the 6th day or 7th day of culture ($\times 400$), the small photograph is the enlarged photograph of the specific cell ($\times 2$).

D: a microscopic photograph of the dendritic cells which are forming specific small and long protrusions on the 9th day of culture ($\times 1000$), the small photograph is the enlarged photograph of the specific cell ($\times 2$).

Figure 4:
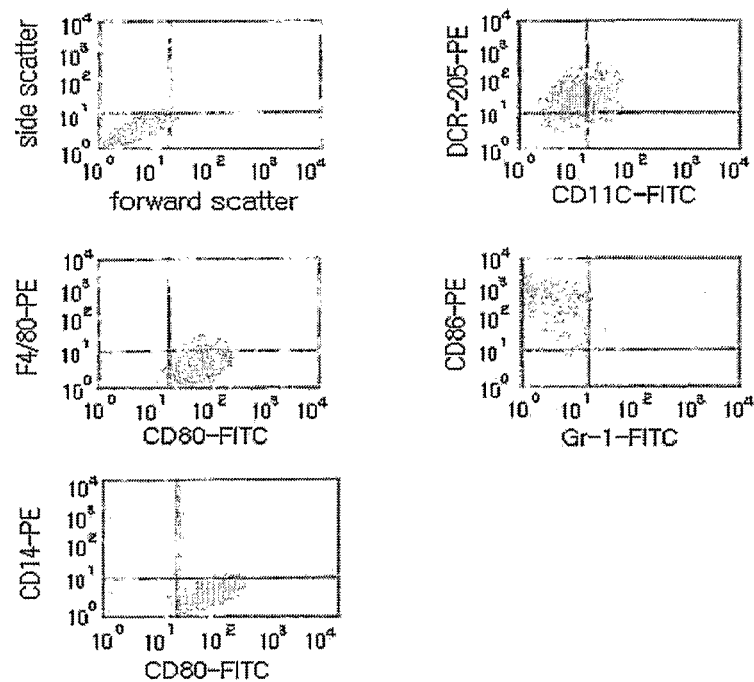

FIG. 4 is a set of graphs showing the results of FACS analyzing the expressions of the dendritic cell specific markers, a monocyte specific marker and a granulocyte specific marker on the 11th day of culture of bone marrow cells separated from Balb/c AnN mouse. (Here, staining of isomer control against hamster's IgG and rat's IgG2a is used for a setting marker line (straight line).

Following markers are used:

CD80 and CD86 as co-stimulation specific markers,

CD11c and DEC-205 as dendritic cell specific markers,

CD14 and F4/80 as monocyte/macrophage specific markers,

Gr-1 as a granulocyte specific marker.

Figure 5:
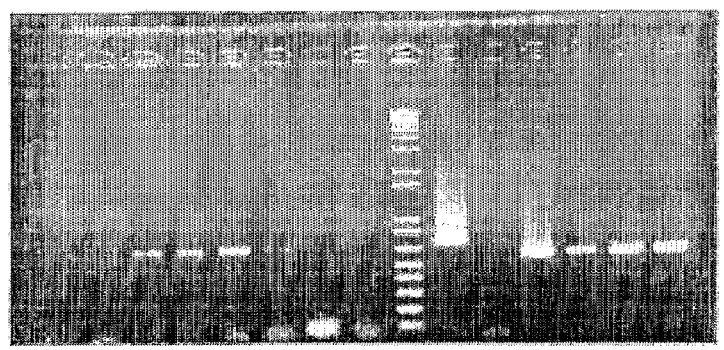

FIG. 5 is an electrophoresis photograph showing the effects of Compound 3 on dendritic cells on the expression of adhesion molecules.

| Lane 1: Vcam-1 | Lane 2: Icam-1 | Lane 3: Icam-2 |
| Lane 4: VLA-4 | Lane 5: VLA-5 | Lane 6: LFA-1 |
| Lane 7: GAPDH | | |

(+): Compound 3 treated group
(−): Control group.

Figure 6:
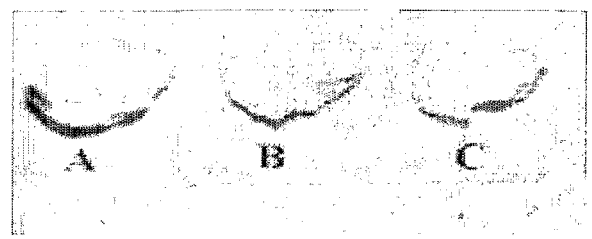

FIG. 6 is a set of photographs showing the results of tumor forming at the near injection site, 4 weeks after tumor (KIGB-5) i.v. injection and processing with different condition.

| A: RPMI control group | B: BMSC treated group |
| C: BMSC + Ad/ΔE1 treated group. | |

Figure 7:

FIG. 7 is a set of photographs showing the results of tumor forming at the near injection site, 8 weeks after tumor (KIGB-5) i.v. injection and processing with different condition.

A: RPMI control group

B: BMSC ($2.5 \times 10^6$ cells/day) treated group

C: BMSC ($2.5 \times 10^6$ cells/day)+Ad/ΔE1 (50 MOI) treated group

D: Dendritic Cells ($5 \times 10^6$ cells/day)+Tumor lysate treated group

E: BMSC ($2.5 \times 10^6$ cells/day)+Ad/IL-2 (50 MOI) treated group

F: Compound 3 (50 mg/kg/day) treated group.

Figure 8:
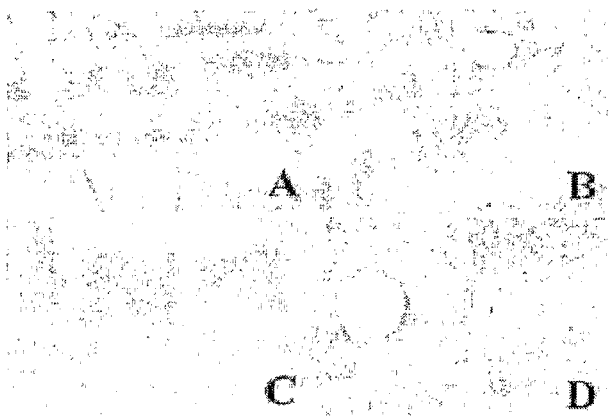
Figure 9:

FIGS. 8 and 9 are a set of photographs showing the gross and microscopic findings of metastatic lung lesions of each group, 8 weeks after tumor (KIGB-5) i.v. injection.

In FIG. 8,

A: RPMI control group

B: BMSC ($2.5 \times 10^6$ cells/day) treated group

C: BMSC ($2.5 \times 10^6$ cells/day)+Ad/ΔE1 (50 MOI) treated group

D: BMSC ($2.5 \times 10^6$ cells/day)+Ad/IL-2 (50 MOI) treated group.

In FIG. 9,

A: RPMI control group

B: Dendritic Cells ($5\times10^6$ cells/day)+Tumor lysate treated group

C: Compound 3 (25 mg/kg/day) treated group.

Figure 10:
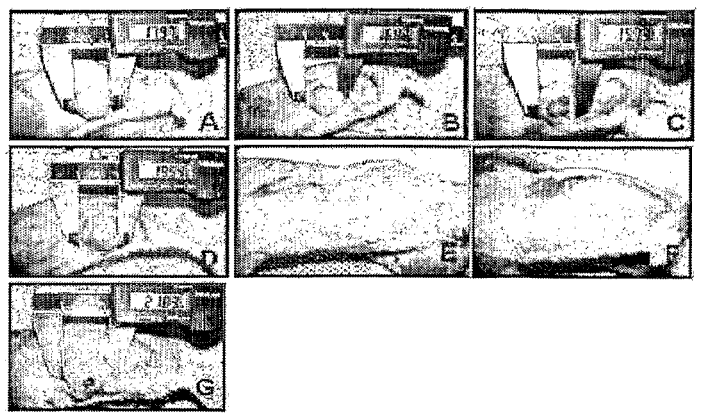

FIG. 10 is a set of photographs showing the lung tumors and its size of each group, 12 weeks after tumor (KIGB-5) s.c (subcutaneously) injection.

A: RPMI control group

B: BMSC ($2.5\times10^6$ cells/day)+Ad/ΔE1 (50 MOI) treated group

C: BMSC ($2.5\times10^6$ cells/day) treated group

D: DC ($5\times10^6$ cells/day)+Tumor lysate treated group

E: BMSC ($2.5\times10^6$ cells/day)+Ad/IL-2 (50 MOI) treated group

F: BMSC ($2.5\times10^6$ cells/day)+Ad/IL-2 (50 MOI)+Compound 3 (25 mg/kg/day) treated group G: Compound 3 (25 mg/kg/day) treated group.

Figure 11:
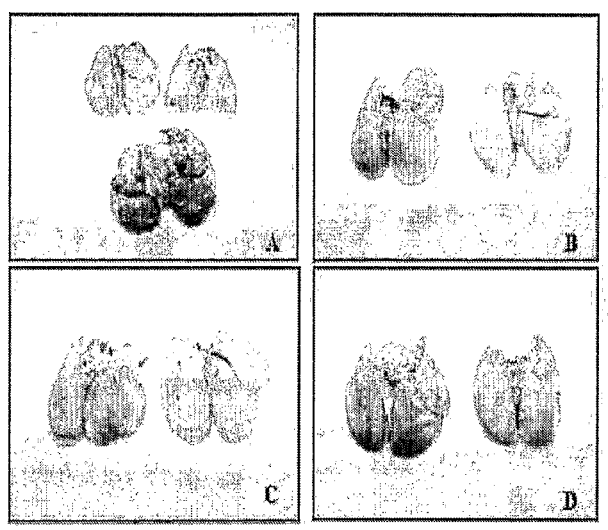

FIG. 11 is a set of photographs showing gross findings of metastatic lung lesions of each group of Syrian golden hamsters treated with various doses of Compound 3, 8 weeks after biliary cancer cell (($5\times10^5$ cells) injection.

A: PBS Control group

B: Compound 3 (10 mg/kg/day) treated group

C: Compound 3 (25 mg/kg/day) treated group

D: Compound 3 (50 mg/kg/day) treated group

Figure 12:
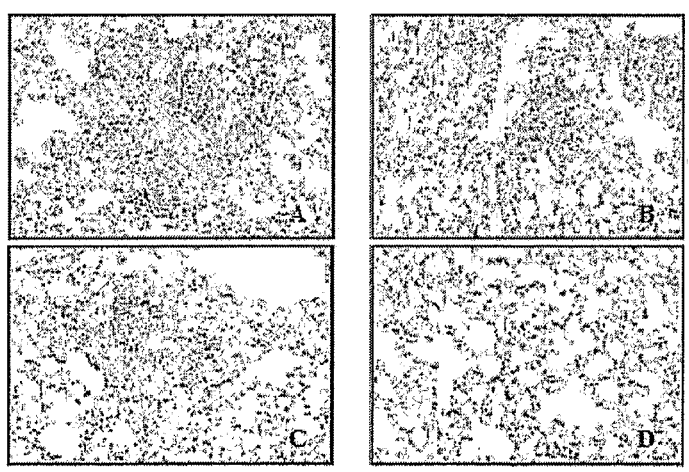

FIG. 12 is a set of photographs showing microscopic findings of metastatic lung lesions of each group of Syrian golden hamsters treated with various doses of Compound 3, 8 weeks after biliary cancer cell (($5\times10^5$ cells) injection.

A: PBS Control group

B: Compound 3 (10 mg/kg/day) treated group

C: Compound 3 (25 mg/kg/day) treated group

D: Compound 3 (50 mg/kg/day) treated group

Figure 13:
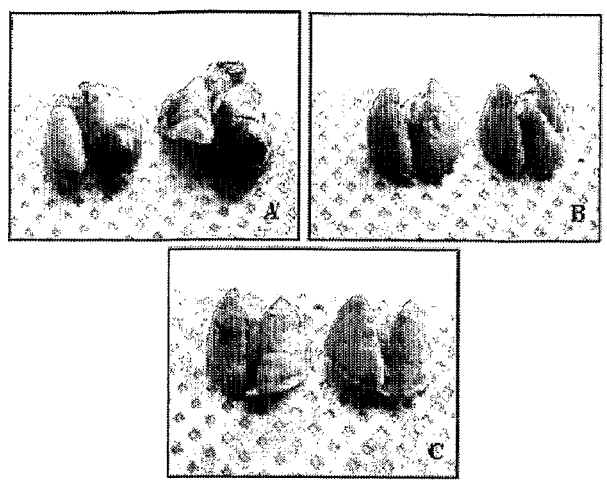

FIG. 13 is a set of photographs showing gross findings of metastatic lung lesions of each of C57B1/6 mice received various treatments, 4 weeks after melanoma cells ($2\times10^4$ cells) i.v. injection.

A: PBS Control group

B: Dendritic cells ($4\times10^5$ cells/day)+tumor lysate treated group

C: Compound 3 (50 mg/kg/day) treated group.

Figure 14:
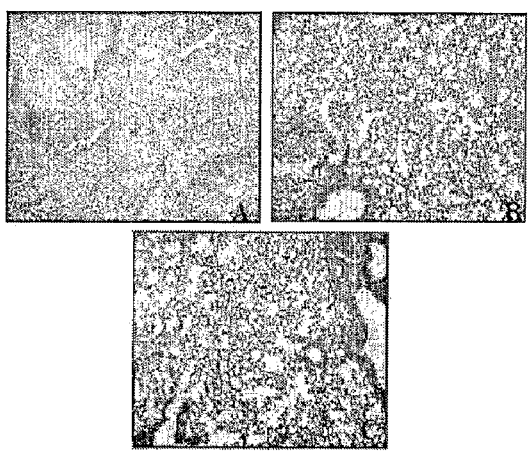

FIG. 14 is a set of photographs showing microscopic findings of metastatic lung lesions of each of C57B1/6 mice received various treatments, 4 weeks after melanoma cells ($2\times10^4$ cells) i.v. injection.

A: PBS Control group

B: Dendritic cells ($4\times10^5$ cells/day)+tumor lysate treated group

C: Compound 3 (50 mg/kg/day) treated group.

Figure 15:
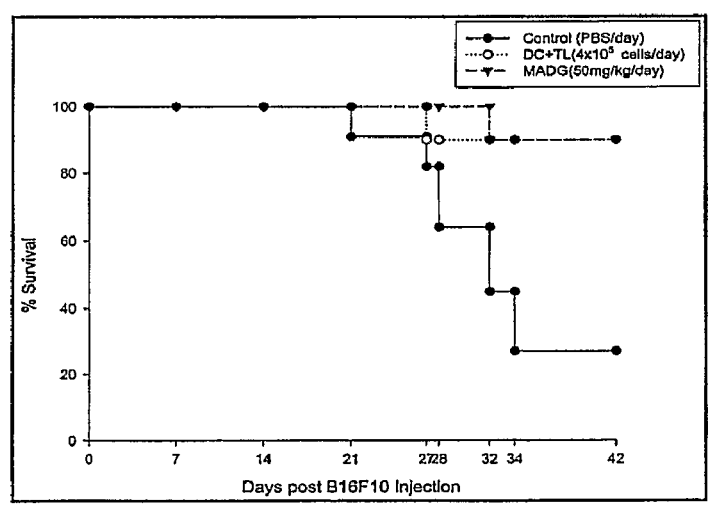

FIG. 15 is a graph showing survival rate of each treated group during 6 weeks after melanoma cells ($2\times10^4$ cells) i.v. injection.

① RPMI control group

② Dendritic cells ($5\times10^5$ cells/day)+tumor lysate treated group

③ Compound 3 (50 mg/kg/day) treated group.

Figure 16:
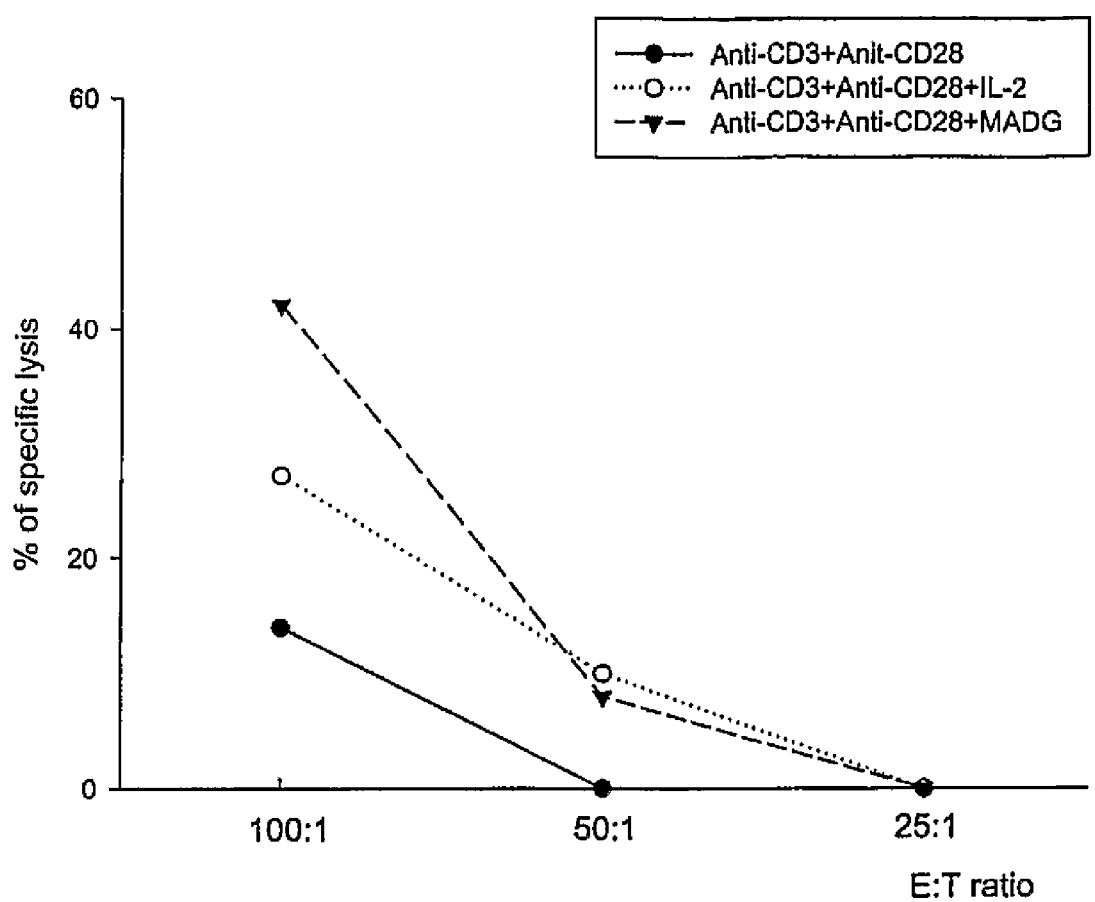

FIG. 16 is a graph showing the cytotoxicity of T lymphocytes activated by Compound 3 on melanoma cells ① Control 1: anti-CD3, anti-CD28 treated group ② Control 2: anti-CD3, anti-CD28, and IL-2 (20 ng/ml) treated group ③ Experimental group: anti-CD3, anti-CD28, and Compound 3 (1 μg/ml) treated group.

MODE FOR INVENTION

Hereinafter, the present invention is described in detail.

The present invention provides an immunomodulating agent, an AIDS treatment, a sepsis treatment, and an anticancer agent containing mono acetyl diacyl glycerol derivatives represented by the following formula 1 as an effective ingredient. The compound represented by formula 1 of the present invention is one of following 5 compounds:

1) 1-oleoyl-2-2palmitoyl-3-acetylglycerol(R1/R2=9-octadecenoyl/hexadecanoyl, referred as "Compound 1" hereinafter)

2) 1-palmitoyl-2-oleoyl-3-acetylglycerol(R1/R2=hexadecanoyl/9-octadecenoyl, referred as "Compound 2" hereinafter)

3) 1-palmitoyl-2-linoleyl-3-acetylglycerol(R1/R2=hexadecanoyl/9,12-octa decadienoyl, referred as "Compound 3" hereinafter)

4) 1-palmitoyl-2-linolenoyl-3-acetylglycerol(R1/R2=hexadecanoyl/9,12,15-octadecatrienoyl, referred as "Compound 4" hereinafter)

5) 1-palmitoyl-2-arachidonoyl-3-acetylglycerol(R1/R2=hexadecanoyl/5,8,11, 14-eicosatetraenoyl, referred as "Compound 5" hereinafter)

Any of mono acetyl diacyl glycerol derivative represented by formula 2 is available and in particular, Compound 3 is preferred. The compound of the present invention was extracted from C.N. antlers or manufactured by conventional organic synthesis method. The exemplary of extraction method has the following steps. Particularly, the chloroform extracts of C.N. antler are obtained by extracting C.N. antler with hexane first and further extracting the residue of the hexane extract with chloroform. The amounts of hexane and chloroform used in this extraction process are enough amounts to impregnate deer antler. Generally, hexane and chloroform are used in the ratio of 4~5 l to 1 kg of C.N. antler. The chloroform extract of C.N. antler obtained from such extraction processes, is fractionated and purified by a series of silica gel column chromatography and TLC (Thin layer chromatography). An eluent of the subsequent extracting steps is selected from chloroform/methanol, hexane/ethylacetate. In order to synthesize mono acetyl diacyl glycerol derivatives chemically, for instance, 1-palmitoylglycerine is separated from the products in the reaction of both glycerol and palmitic acid. The objecting mono acetyl diacyl glycerol can be synthesized as esterifying 1-palmitoylglycerine with carboxylic acid compounds such as acetic acid and linoleic acid, and purified as occasion demands. Another method for synthesizing mono acetyl diacyl glycerol derivatives is the acetolysis of phosphatidyl choline.

The mono acetyl diacyl glycerol compound according to the present invention is for immunomodulating agent. Immunity modulation includes increasing deteriorated immunity abnormally or maintaining the balance of increased immunity abnormally. Therefore, mono acetyl diacyl glycerol compounds according to the present invention have effects of not only preventing and treating various diseases resulted from deteriorated immune system and caner but also inhibiting, preventing, and treating autoimmune diseases such as arthritis, atopy, dementia, and sepsis resulted from autoimmune reaction.

In the regulation of immune function, the important thing is not increase of T cell which is responsible for immunity but the extent of T cell's activation, the ratio of T4 to T8 cells, and the kinds of cytokines secreted from T4 and T8 cells. The present inventors treated mono acetyl diacyl glycerol derivatives to T-4 and T-8 lymphocytes for researching the immunomodulating effect of mono acetyl diacyl glycerol derivatives of the invention. As a result, it was confirmed that secretion of IL-2, a kind of cytokines, was increased in those cells (see FIG. 1). After treating the cells with the Compound 3 of the present invention by using Bio-plex, which enables measuring huge amount of cytokines at a time, the secretion of cytokine in T-cells was investigated. As a result, the secretions of IL-2, IL-4, and IL-5 were much greater in Compound 3 treated group than in a control group (see FIG. 2). The most increased cytokine, IL-4 is a multi-function cytokine called anti-inflammation cytokine which is secreted from Th2 which is differentiated from T4 cells. As inhibiting differentiation of T4 to Th1, IL-4 can suppress cell damage resulted from autoimmune reaction by processing important role to anti-cancer effect and immune response regulation (Annu. Rev. Immunol. 1999. 17: 701~738). The compounds of the present invention have effects of both immunity enhancing by stimulating IL-2 secretion and immunity modulating by stimulating IL-4 secretion. And, the compounds of the present invention also can maintain the ratio of T4 to T8 normally by increasing and activating not only T4 but also T8, which is a cytotoxic immune cell. Therefore, it is effective for treating on side effects and diseases resulted from abnormal increasing or decreasing of immune system. In the septic shock model, these immunity enhancing effects can work to the direction of stimulating IL-4 secretion and inhibiting apoptosis. In result, the lethal rate of sepsis is decreased remarkably. Therefore, mono acetyl diacyl glycerol derivatives according to the present invention are useful for the treatment of autoimmune diseases, for instance the preventing and treating of sepsis, because these compounds increase IL-4 secretion.

It has been known to that the interaction between cells stimulate various hematopoietic cells and immune cells, and particularly, dendritic cells are very important in immune system. The present inventors investigated the effect of mono acetyl diacyl glycerol derivatives on the interaction between separated and induced dendritic cells and TCR (T-cell Receptor). For the investigation, RT-PCR of the Compound 3 treated DC (Dendritic Cells) was performed to measure the expressions of adhesion molecules mediating the interaction between DC and TCR. As a result, the expression of adhesive molecules such as Vcam-1, Icam-1, Icam-2, VLA-4, VLA-5, and LFA-1 were increased, comparing to a control (see FIG. 5). From the above results, mono acetyl diacyl glycerol derivatives according to the present invention were confirmed to have the effects not only T-cell activation effect but also specific anti-cancer effect through activating of dendritic cells which enable T-cell to recognize antigen of cancer cells.

From the above results, mono acetyl diacyl glycerol derivatives according to the present invention were confirmed to have the immunity enhancing effect by increasing cytokine secretion through activating T-cells and by promoting the proliferation and stimulation of hematopoietic cells and immune cells through increasing the expressions of intracellular adhesion molecules. As a result, it was confirmed that these compounds have the possibility of using as an immunotherapy against various diseases. For instance, mono acetyl diacyl glycerol derivatives according to the present invention can be used as treatment or health food for enhancing immunity in human AIDS patients by the proliferation effect of T4 and T8 cells. In the early phase of the AIDS patients, T4 was decreased but serious outbreak did not happen. On the other hand, in the late phase of the AIDS patient, T8 was decreased and serious outbreak happened. Therefore, the ratio of T4 to T8 is an important factor and the absolute number of T4 and T8 is also an important factor. Further, the present inventors confirmed that the modulation of immune function by the increasing of the IL-4 secretion is effective for various autoimmune diseases. In order to investigate the use of compounds according to the present invention as prevention and treatment for septic shock, the CLP (Cecal Ligation and Puncture) test of mice was performed. In result, all tested mice survived until 120 hours. Therefore, it confirmed that mono acetyl diacyl glycerol derivatives according to the present invention were effective for preventing and treating of sepsis. From the above results, it confirmed that mono acetyl diacyl glycerol derivatives according to the present invention were good for ideal immunomodulating agent having both immunity enhancing effect and immunity function regulation effect.

Further, in order to investigate the use of compounds according to the present invention for prevention and treatment of cancer, the present inventors investigate anti-cancer effect of the compounds against biliary cancer and malignant melanoma that were known to the incurable cancer. First, the present inventors induced cancer in a hamster by injecting intravenously or subcutaneously KIBG-5, a biliary cancer cell line. Then, RPMI, BMSC, adenovirus/ΔE1, dendritic cell+tumor lysate, Compound 3, adenovirus/IL-2 and the mixtures were injected to a hamster. The observation of result was performed 4 weeks later. As a result, when it observed by the naked eye or a microscope, dendritic cell+tumor lysate, Compound 3, and adenovirus/IL-2 treated groups did not form tumor (see FIG. 6). Further, tumor cells were injected intravenously and observation was performed 8 weeks later. As a result, metastatic lung lesion was formed in all groups except BMSC+adenovirus/IL-2 treated group. From the biopsy, only a minute lesion was observed in dendritic cell+tumor lysate treated group and Compound 3 treated group (see FIG. 7, FIG. 8, and FIG. 9). And further, tumor cells were injected subcutaneously and observation was performed 12 weeks later. As a result, tumor was formed in all groups except BMSC+adenovirus/hIL-2 treated group and BMSC+Ad/hIL-2+Compound 3 treated group (see FIG. 10). The tumor formation was inhibited by Compound 3 dose-dependently (see FIGS. 11 and 12). As explained hereinbefore, the present inventors induced metastatic cancer in hamster by injecting biliary cancer cells (KIBG), and then treated the hamster with mono acetyl diacyl glycerol derivatives of the present invention. As a result, it was confirm that cancer development was significantly inhibited by the treatment of those compounds of the present invention.

Intravenous injection of malignant melanoma cells was performed to the tail of mice to induce cancer therein. Then, each of or the mixture of RPMI, dendritic cells (DC), tumor lysate and Compound 3 was treated. As a result, metastatic lung lesion was formed in a control group treated with RPMI, but no lesions were observed in the groups each treated with Compound 3 and dendritic cells+tumor lysate (see FIGS. 13 and 14). In addition, Compound 3 treated group and dendritic cells+tumor lysate treated group were observed for 6 weeks after tumor injection, resulting in 90% survival rate (see FIG. 15). Based on the above results, the present inventors confirmed that Compound 3 activates T-cell (T4 and 8), which means it has anti-cancer effect. So, the present inventors performed cytotoxicity test of T-cells activated by Compound 3 to malignant melanoma in vitro. As a result, cytotoxicity was increased much when T-cells were treated with Compound 3 than when T-cells were not treated with Compound 3, and also cytotoxicity was increased with the increase of the amount of T-cells (see FIG. 16). As explained hereinbefore, it was confirmed that mono acetyl diacyl glycerol derivatives of the present invention inhibit cancer development and show cytotoxicity to cancer cells by activating T-cells, indicating that the compounds of the present invention can be effectively used as an anti-cancer agent. The treatment with the product of the present invention as an anti-cancer agent appears to be promising for bile duct cancer, kidney cancer and melanoma, but other forms of malignant diseases should be explored.

The present inventor, henceforth, completed this invention by preparing trial capsules and tablets containing mono acetyl diacyl glycerol derivatives as an effective ingredient. An immunomodulating agent, an AIDS treatment, a sepsis treatment, and an anti-cancer agent of the present invention preferably include mono acetyl diacyl glycerol derivatives by 20 to 100 weight % to the total weight of compounds, more preferably include them by 30 to 100 weight %. If the amount of mono acetyl diacyl glycerols is too much or less, it just difficult to take medicine and there are no advantages. It is also preferred for a sepsis treatment, an anti-cancer agent, and an immunomodulating agent to be orally administered 1 to 3 times/day or 1 to 4 times/day with the dose of 50 mg/kg. The compounds according to the present invention can additionally include one or more pharmaceutically acceptable carriers, in addition to an effective ingredient, to be formulated in a pharmaceutical form. The carrier can be selected from a group consisting of saline, buffered saline, water, glycerol and ethanol, but the selection is not always limited thereto. Any acceptable pharmaceutical formulation know in this field (Remingtons Pharmaceutical Science (the latest edition), Mack Publishing Company, Easton Pa.) is available. A composition of the present invention can be administered orally and be used in general forms of pharmaceutical formulations. The composition of the present invention can be prepared for oral administration by mixing with generally used fillers, extenders, binders, wetting agents, disintegrating agents, diluents such as surfactant, or excipient. The effective dosage of the composition of the present invention can be determined according to age, gender, health condition, absorption of an active ingredient, inactivation rate, excretion and other medicines applied together. For example, the dosage for oral administration might be 0.24 to 9.0 g per day, but not always limited thereto. The present invention also includes pharmaceutical formulations in dosage units. This means that the formulations are presented in the form of individual parts, for example tablets, coated tablets, capsules, pills, suppositories and ampoules, the active compound content of which corresponds to a fraction or a multiple of an individual dose. The dosage units can contain, for example, 1, 2, 3, or 4 individual doses or ½, ⅓, or ¼ of an individual dose. An individual dose preferably contains the amount of active compound which is administered in one application and which usually corresponds to a whole, ½, ⅓ or ¼ of a daily dose. Solid formulations for oral administration are tablets, pills, dusting powders and capsules, liquid formulations for oral administration are suspensions, solutions, emulsions and syrups, and the above mentioned formulations can contain various excipients such as wetting agents, sweeteners, aromatics and preservatives in addition to generally-used simple diluents such as water and liquid paraffin. The compounds of the present invention can be applied not only formulations for oral administration but also formulation for injection. For example, watery or oily suspension for sterile injection can be prepared according to the known method with dispersing agents, wetting agents or emulsions. Any acceptable pharmaceutical solvent includes water, Ringer's solution, or isotonic NaCl solution. Sterile fixing oil is used as solvent or dispersive medium and can include non-stimulus fixing oil including monoglyceride, diglyceride, and poly propylene glycol and fatty acid such as oleic acid.

The present invention also provides immunomodulating and anti-cancer health food containing mono acetyl diacyl glycerol derivatives as an effective ingredient. In the present invention, "health food" includes foodstuff, nutrient and health supplement for treating or preventing of various diseases and maintaining the balance of body function. Health food prepared in the present invention contains mono acetyl diacyl glycerols by 0.02 to 100 weight %. In the case of using the compounds of the present invention as health food, the compounds can be used according to the conventional method, for example, using intact compounds or using mixed compounds with other foods or food ingredients. The effective amount of the compound mixture depends on the purpose of its use (prevention, health or therapeutic treatment). In the case of using for prevention, the preferable amount of mono acetyl diacyl glycerol derivatives is from 0.02 to 2 weight % for the total amount of health food, preferably 0.2 to 0.6 weight %. If the amount of mono acetyl diacyl glycerols is too much or less, it just difficult to take health food and there are no advantages. The effective ingredient is also safe for the long-term administration aiming at the control or the preservation of health, supported by cytotoxicity test. Any kinds of food containing the composition of the present invention can be made without limitation. For example, meat sausage, bread, soups, beverages, teas, drinks, alcoholic beverages and vitamin complex are the food to be made as health food containing the composition of the present invention. In case that the health food is used as nutrients or health supplements for the purpose of treating and preventing disease, the preferable amount of mono acetyl diacyl glycerol derivatives is from 20 to 100 weight % for the total amount of health food, preferably 30 to 100 weight %, more preferably 35 to 95 weight. The intake might be 0.18 to 9.0 g per day, but not always limited thereto. The formulations include tablets and capsules.

As explained hereinbefore, mono acetyl diacyl glycerol derivatives of the present invention activate T-cells to promote the secretion of cytokines, increase the expression of adhesive molecules between cells to stimulate hematopoietic cells and immune cells so as to not only improve immunity but also prevent and treat autoimmune disease and cancer.

Hereinafter, the preferable experimental examples are provided for better understanding of the present invention. However, the present invention is not limited to the following experimental examples.

EXPERIMENTAL EXAMPLE 1

Effects of Mono Acetyl Diacyl Glycerol Derivatives on T-Cell and Mononuclear Cell Proliferation

EXPERIMENTAL EXAMPLE 1-1

Effects of Mono Acetyl Diacyl Glycerol Derivatives on T-Cell Proliferation

Splenocytes were collected from C57BL/6 mice (provided from Asan Institute for Life Sciences Animal Lab., Seoul, Korea) spleens. Then, single cell suspensions were obtained by repeated aspiration and flushing. Red blood cells were removed using ammonium chloride and then passed through nylon wool to remove debris and clumps. T-cells were purified using magnetic bead (MACS bead, Miltenyi Biotec, bergich gladbach, Germany) containing anti-goat IgG MACS bead, Miltenyi Biotec, bergich gladbach, Germany) or anti-mouse CD4 (MACS bead, Miltenyi Biotec, bergich gladbach, Germany) or anti-mouse CD8 antibody (MACS bead, Miltenyi Biotec, bergich gladbach, Germany) (Turner and Dockrell (1996) Immunology, 87: 339-342).

T cell suspensions were suspended in Isocove's modified Dulbecco's medium (IMDM, Gibco, Grand Island, N.Y.) supplemented with 10% fetal bovine serum (referred as 'FBS' hereinafter) (Gibco, Grand Island, N.Y.). $5 \times 10^4$ viable cells per well were cultured in 96-well plates, with 1 μg/ml, of Compound 1, Compound 2, Compound 4 and Compound 5, 0.01, 0.1, 1 μg/ml of Compound 3 (synthesized and provided by Department of Chemistry, Ewha Womans University, Seoul, Korea) or 20 ng/ml of IL-2. On the 6th day, cells were incubated with 1 μCi $^3$H-thymidine/well for 24 hours. On the $7^{th}$ day, the cells were harvested and the incorporation Index (referred as 'SI' hereinafter) was calculated by the following Mathematical Formula 1.

$SI=$$^3$H-thymidine absorbed by wells of experimental group (CPM in sample)/$^3$H-thymidine absorbed by wells of control group (CPM in control) [Mathematical Formula 1]

As a result, mono acetyl diacyl glycerol derivatives treated group had increased Si of T-cells by thymidine uptake of 2.05, which was similar to that of IL-2 treated group (Table 1).

TABLE 1

| Treated group | SI |
|---|---|
| IL-2 (20 ng/ml)* | 2.05 ± 0.24 |
| Compound 1 (1 μg/ml)* | 2.01 ± 0.43 |
| Compound 2 (1 μg/ml)* | 2.03 ± 0.54 |
| Compound 3 (0.01 μg/ml)** | 1.83 ± 0.32 |
| Compound 3 (0.1 μg/ml)* | 1.96 ± 0.18 |
| Compound 3 (1 μg/ml)* | 2.05 ± 0.64 |
| Compound 4 (1 μg/ml)* | 1.98 ± 0.26 |
| Compound 5 (1 μg/ml)* | 2.02 ± 0.38 |

*P < 0.05,
**P < 0.005.
All tests were done in triplicate and were repeated three times.

EXPERIMENTAL EXAMPLE 1-2

Effects of Mono Acetyl Diacyl Glycerol Derivatives on Monocytes Proliferation

Monocytes were isolated from human whole blood using Histopaque 1077. And then, monocytes ($5 \times 10^6$ cells/ml) were allowed to adhere to tissue culture flask for 3 hours in a 5% $CO_2$ incubator. After 3 hours, non-adherent cells were removed and adherent cells were placed in 96-well plates in RPMI 1640 medium (GIBCO, Grand Island, N.Y.) supplemented with 10% FBS. $5 \times 10^4$ viable cells per well were cultured in 96-well plates, with 1 μg/ml of Compound 1~5. On the $6^{th}$ day, cells were incubated with 1 μCi $^3$H-thymidine/well for 24 hours. On the $7^{th}$ day, the cells were harvested and the incorporation of $^3$H-thymidine was measured. Si was calculated by the above mentioned formula 1. As a result, Compound 1-5 treated group had increased monocytes SI 10.68, comparing to control, indicating that the compounds stimulated proliferation of monocytes (Table 2).

TABLE 2

| Treated group | SI (±S.E) |
|---|---|
| Non treated control | 1 |
| Compound 1 (1 μg/ml)* | 9.97 ± 0.10 |
| Compound 2 (1 μg/ml)* | 10.42 ± 0.15 |
| Compound 3 (1 μg/ml)* | 10.68 ± 0.13 |
| Compound 4 (1 μg/ml)* | 10.21 ± 0.18 |
| Compound 5 (1 μg/ml)* | 9.75 ± 0.09 |

*P < 0.001,
All tests were done in triplicate and were repeated two times.

EXPERIMENTAL EXAMPLE 2

Effects of Compound 3 on T Cell Activity

EXPERIMENTAL EXAMPLE 2-1

Measurement of Cytokine by Elispot

Figure 1:
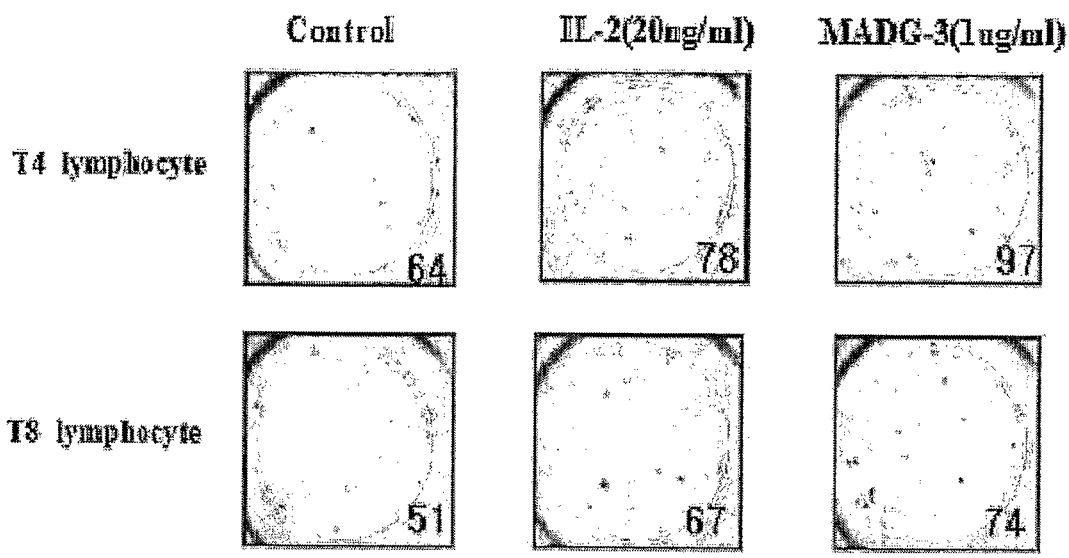
FIG. 1 is a set of photographs showing the T-cell (T-4 and T-8) activity of control group, IL-2 treated group (20 ng/ml), and Compound 3 treated group (1 μg/ml). Each number indicates the number of spots capturing IL-2 specific antibody.

Elispot bioassay (ESAT-6 enzyme-linked immunospot assay) is a very sensitive quantification assay for detecting cytokine bound to the membrane because the bottom of each well of Elispot plates used in this assay was pre-coated with a cytokine specific antibody. Thus, Elispot assay was performed to measure the T cell activity. T-cells were seeded by $2 \times 10^6$ cells to each well in a 24-well sterile tissue culture plate (Nunc, Denmark), followed by the treatment with 0.01, 0.1, 1 μg/ml concentrations of Compound 3 or IL-2 (20 ng/ml). On the $7^{th}$ day, cells were harvested and the cells were seeded by $5 \times 10^5$ cells/ml in multi-testplates (Elispot system kit, AID, Straberg, Germany) coated with the respective primary antibody (murine IL-2). After the plate was incubated for 24 hours in a 5% $CO_2$ incubator, there was a secretion of cytokines by the cells, which were captured by the primary antibody (murine IL-2) determined by Elispot using commercially available mouse IL-2 Elispot kits according to the manufacturer's instructions. Each sample was tested in duplicate. Counting the number of IL-2 producing cells by Elispot is accomplished with Elispot reader (AID Elispot Reader System). The results showed that Compound 3 treated group showed 1.52 folds increased T-4 activity, comparing to control group, and 1.46 folds increased of T-8 activity (FIG. 1).

EXPERIMENTAL EXAMPLE 2-2

Measurement of Cytokine by Bio-Plex

Figure 2:
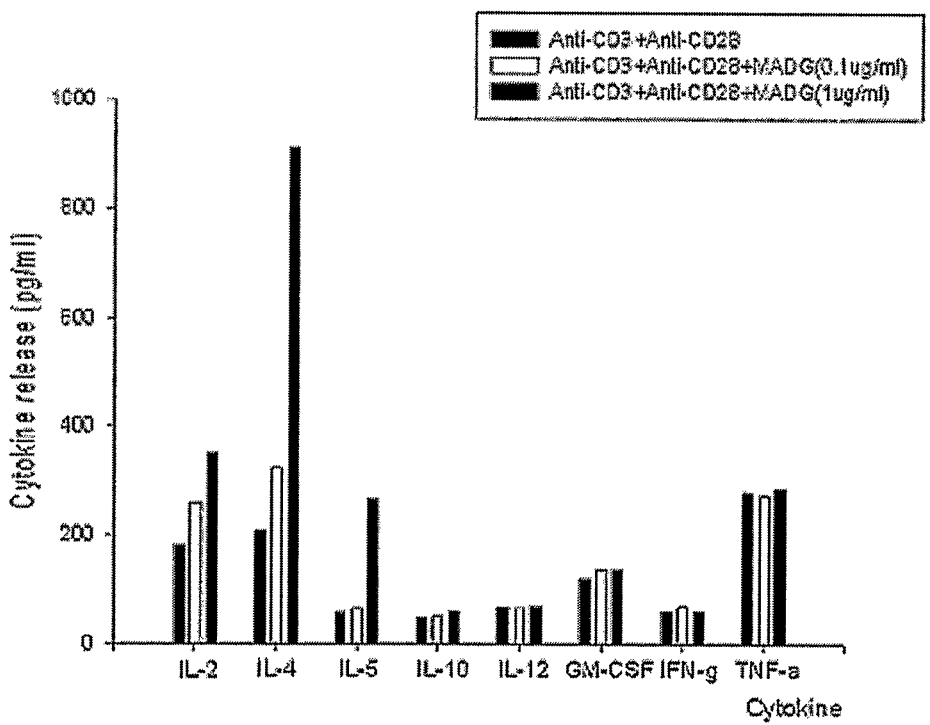
FIG. 2 is a graph showing the release of cytokines when T lymphocytes are activated by Compound 3, ① Control group: anti-CD3, anti-CD28 treated, ② Experimental group: anti-CD3, anti-CD28 and Compound 3 (0.1, 1 μg/ml) treated.

Bio-plex can measure huge amount of cytokine at a time in a well. Thus, Bio-plex kit was used to quantify 8 kinds of cytokines of Th1/Th2 channels, which are secreted when T-cells are activated. Sterilized 24-well tissue culture plate (Nunc, Denmark) was treated with anti-CD3 and anti-CD28. Then, the plate was inoculated with T-cells by $2 \times 10^6$ cells/ml. In order to activate T-cells, 0.1, 1 μg/ml of Compound 3 was treated thereto, followed by culture for 5 days. On the $5^{th}$ day, culture solutions at each different stage were recovered, followed by centrifugation. Supernatants were obtained and cytokine secreted therein was quantified by using Bio-plex kit according to the manufacturer's instruction (Bio-rad). As a result, three kinds of cytokines (IL-2, IL-4, and IL-5), among 8 kinds of cytokines (IL-2, IL-4, IL-5, IL-10, IL-12, INF-γ, GM-CSF, TNF-α) were secreted in the group treated with Compound 3 and the amounts of them were bigger than those in a control group not treated with Compound 3 (FIG. 2).

EXPERIMENTAL EXAMPLE 3

T Cell Proliferation Assay

The following experiment was performed to confirm the effect of Compound 3 against immunocytes of the AIDS patients. First, Human mononuclear cells were obtained by Hisopaque 1077 from peripheral blood of AIDS patients. Red blood cells were removed using ammonium chloride and then passed through nylon wool to remove debris and clumps. T-cells were purified using magnetic bead (anti-human CD3) (MACS bead, Miltenyi Biotec, bergich gladbach, Germany). T cell suspensions were suspended in Isocove's modified Dulbecco's medium (IMDM, Gibco, Grand Island, N.Y.) supplemented with 10% fetal bovine serum (referred as 'FBS' hereinafter) (Gibco, Grand Island, N.Y.). $5 \times 10^4$ viable cells per well (in triplicate) were cultured in 96-well plates, with 0.01, 0.1, 1 µg/ml concentrations of Compound 3 or IL-2 (20 ng/ml). On the 6th day, cells were incubated with 1 µCi $^3$H-thymidine/well for 24 hours. On the $7^{th}$ day, the cells were harvested and the incorporation of $^3$H-thymidine was measured. The SI (Stimulation Index) was calculated by the above mentioned formula 1. As a result, in AIDS patients, T cell proliferation assay, showed Compounds 3 treated group had 1.5 to 3.9 fold increase of T-cell stimulation index by thymidine uptake in all patients (4 out of 4) compared with control as seen in Table 3. Over all result of stimulation by Compound 3 was comparable with IL-2 stimulation.

TABLE 3

| | Stimulation Index (SI) | | | |
|---|---|---|---|---|
| | 1 | 2 | 3 | 4 |
| IL-2(20 ng/ml) | 1.41 | 4.17 | 1.29 | 6.54 |
| Compound 3 (1 µg/ml) | 2.23 | 3.87 | 1.48 | 3.49 |

EXPERIMENTAL EXAMPLE 4

Effects of Compound 3 on the Expression of Adhesion Molecules of Dendritic Cells

EXPERIMENTAL EXAMPLE 4-1

Dendritic Cell Culture

Figure 3:
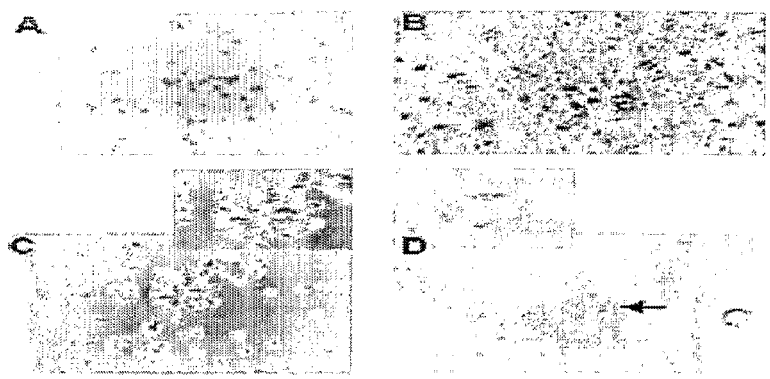
FIG. 3 is a set of photographs showing the morphology of mouse dendritic cells derived from mouse bone marrow cells after the treatment of GM-CSF (20 ng/ml), IL-4 (20 ng/ml) and TNF-α (5 ng/ml).

Bone marrow cells were obtained from the femurs and tibias of Balb/c AnN mice (Park, J. et al. (2003) *J. Korean Med. Sci.*, 18: 372-380). The cells were washed 3 times in RPMI, and then mononuclear cells were obtained. These mononuclear cells were allowed to adhere to tissue culture flask 3 hours in RPMI and 10% FBS. After incubation, the adherent cells (monocytes) were removed and non-adherent cells were placed in 100 mm tissue culture dishes, in a concentration of $1 \times 10^5$ cells/ml in RPMI plus 10% FBS supplemented with 20 ng/ml murine rGM-CSF (R & D systems, Minneapolis, Minn., USA), 10 ng/ml, murine IL-4 (R&D systems), and 2.5 ng/ml murine TNF-α (R & D systems). Culture dishes were fed every 3 days. Murine TNF-α (R & D systems) was added at the $6^{th}$ day of the culture. After that, murine TNF-α (R & D systems) was added every 3 days until on the 11th day. Mature dendritic cells were harvested for RT-PCR of adhesion molecule studies. As a result, when round shaped granulocytes were cultured for three days, those cells formed a cluster which was growing on the bottom of a well of cell culture plate, and mature dendritic cells were growing with forming a group on the $6^{th}$ or the $7^{th}$ day of culture. And on the $9^{th}$ day of culture, dendritic cells formed a small but long protrusion specifically (FIG. 3).

EXPERIMENTAL EXAMPLE 4-2

Determination of Dendritic Cell Phenotype

Those cells that were big and negative against trypan blue staining were counted and the morphology of each of them was investigated. $1 \times 10^6$ cells/ml were cultured and then washed, followed by fixation with 1% para-formaldehyde solution. Flow cytometric analysis of the fixed cells was performed by using FACScan (Beckton Dickinson, Mountain View, Calif., U.S.A), leading to the determination of the phenotype using antibodies against the following markers; isotype control against hamster IgG, rat IgG 2a, DC marker: DEC 205 (NLDC-145) and CD 11C, co-stimulatory/adhesion molecule: CD 80 (B7-1) and CD 86 (B7-2), macrophage marker: CD 14 and F4/80, granulocyte marker: Gr-1 (Pharmingen, Hamburg, Germany). As a result, the levels of co-stimulation specific molecular markers CD80 and C86 and dendritic cell specific markers CD11C and DEC-205 were high. On the contrary, the levels of monocytes specific markers CD14 and F4/80 and granulocyte specific marker Gr-1 were low. The results indicate that the dendritic cells separated in the present invention have an exact phenotype of dendritic cells and the purity 97 to 98% (FIG. 4).

EXPERIMENTAL EXAMPLE 4-3

Treatment and the Expression of Adhesion Molecules

It is generally known that the cell-cell interaction is involved in stimulations of various hematopoietic cells and of immune cells. Thus, the present inventors tried to confirm whether or not Compound 3 affects various adhesion molecules of the mentioned cells. Particularly, dendritic cells cultured in the above example were treated with 1 µg/ml of Compound 3, and then RT-PCR was performed.

Following primers: Icam-1 (SEQ. ID. No 1 and No 2), Icam-2 (SEQ. ID. No 3 and No 4), Vcam-1 (SEQ. ID. No 5 and No 6), VLA-4 (SEQ. ID. No 7 and No 8), VLA-5 (SEQ. ID. No 9 and No 10), LFA-1 (SEQ. ID. No 11 and No 12) and GAPDH (SEQ. ID. No 13 and No 14) were used for the RT-PCR. Reaction sets used herein was a mixed solution of 2 µl DNA, 10× buffer solution, 1.5 µl of $MgCl_2$, 2 µl of dNTPs, 0.5 µl of forward primer, 0.5 µl of reverse primer, 0.2 µl of polymerase and 15.8 µl of distilled water.

Total RNA separated from dendritic cells and MS-5, low density cells cultured with oligo(dt)-primer, was reverse-transcribed, and PCR was performed at 94° C. for 30 seconds, 65° C. for 30 seconds and 72° C. for 50 seconds. PCR was performed 34 times at total, and PCR products were doubled every performance. The expressions of adhesion molecules such as Vcam-1, Icam-1, Icam-2, VLA-4, VLA-5, and LFA-1 were confirmed by RT-PCR. For the quantification, PCR with GAPDH was performed to confirm the corresponding cDNA. The results showed that the expressions of adhesion molecules, Icam-2, VLA-5, LFA-1 on Compound 3 treated dendritic cells were significantly increased compared to a control (FIG. 5).

EXPERIMENTAL EXAMPLE 5

Study on Anti-Cancer Effect of the Compound 3 through Subcutaneous Injection (Local Model) and Intravenous Injection (Systemic Model)

EXPERIMENTAL EXAMPLE 5-1

Biliary Cancer Model in Hamster

Six week old female Syrian golden hamsters (Harlan, Indianapolis, India, USA) were housed in specific pathogen free unit. $5 \times 10^5$ KIBG-5 cells (*Molecular therapy*, Vol. 3, No. 4, pp 431-437) suspended in 100 μl of RPMI 1640 serum-free medium were intravenously injected via femoral vein. And $5 \times 10^5$ KIBG-5 cells suspended in 100 μl of RPMI 1640 serum-free medium were subcutaneously injected to the flank of the hamsters. Hamsters injected KIBG-5 were divided into following 7 groups;
1) Control group treated with RPMI medium,
2) Experimental group treated with non-modified BMSC cells ($2.5 \times 10^6$) (*Leukemia & Lymphoma*, Vol. 44, No. 11, pp 1973-1978),
3) Experimental group treated with BMSC cells modified with Ad/ΔE1 50 MOI (*Leukemia & Lymphoma*, Vol. 44, No. 11, pp 1973-1978),
4) Experimental group treated with DC+ tumor lysate ($5 \times 10^6$),
5) Experimental group treated with BMSC cells modified with Ad/hIL-2 50 MOI (*Leukemia & Lymphoma*, Vol. 44, No. 11, pp 1973-1978),
6) Experimental group treated with BMSC cells modified with Ad/hIL-2 50 MOI+Experimental group treated with Compound 3 (25 mg/kg/day),
7) Experimental group treated with Compound 3 (25 mg/kg/day).

One week after the injection of cancer cells to hamsters (BMSC treated group), $2.5 \times 10^6$ of BMSC cells were injected once again to each hamster. In the case of DC+tumor lysate treated group, $5 \times 10^6$ of DC cells and tumor lysate were injected to each hamster (with subcutaneous injection or intravenous injection) at the first, second, third, forth, sixth, eighth week, followed by observation for 12 weeks. In the case of Compound 3 treated group, one week before KIBG-5 cells injection, Compound 3 (25 mg/kg/day) via P.O was continued 2 weeks on and 1 week off for 8 weeks.

As a result, 4 weeks after the cancer cell injection, tumor formed in RPMI treated group which was a control, BMSC treated group, and BMSC+Ad/ΔE1 treated group, but no tumor were found in DC+tumor lysate treated group, Compound 3 treated group, and BMSC+Ad/IL-2 treated group (FIG. 6). Moreover, 8 weeks after the cancer cell injection, multiple metastatic lung lesions were found in RPMI treated group which was a control, BMSC treated group, and BMSC+Ad/ΔE1 treated group, and only one minute lung lesion was found in DC+ tumor lysate treated group, and Compound 3 treated group. But no lesions were found in BMSC+Ad/IL-2 treated group (FIGS. 7, 8, 9). Further, 12 weeks after the cancer cell subcutaneous injection, tumor formed in RPMI treated group which was a control, BMSC treated group, BMSC+Ad/ΔE1 treated group, and DC+tumor lysate treated group, and less 5 mm sized tumor in one mice were found in BMSC+Ad/hIL-2 treated group but no tumor were found in BMSC+Ad/IL-2+Compound 3 treated group (FIG. 10).

In another hand, six week old female Syrian golden hamsters were housed in specific pathogen free unit. KIGB-5 cells ($5 \times 10^5$) suspended in 100 μl of RPMI 1640 serum-free medium were intravenously injected via femoral vein. Hamsters were divided into following 4 groups: 1) PBS control group, 2) Compound 3 (10 mg/kg/day) treated group, 3) Compound 3 (25 mg/kg/day) treated group, 4) Compound 3 (50 mg/kg/day) treated group. One week before tumor cell injection, Compound 3 (10, 25 or 50 mg/kg/day) via P.O was continued 2 weeks on and 1 week off for 12 weeks. Animals of each group were sacrificed at 4, 8, 12 weeks for pathological examination. Gross findings at $4^{th}$ week, tumor developed at injection site in control group, Compound 3 (10, 25 or 50 mg/kg/day) treated groups showed no evidence of tumor. At $8^{th}$ week, control group observed multiple metastatic lesions in both lungs. Compound 3 treated group (25, 50 mg/kg/day) did not show any metastatic lung lesions with naked eye, but Compound 3 treated group (25 mg/kg/day) showed one minute lesion with microscope. Compound 3 treated group (10 mg/kg/day) showed tumor in the left lung (FIGS. 11 and 12).

EXPERIMENTAL EXAMPLE 5-2

Melanoma Model in Mice (C57BL/6)

6 week female C57BL/6 mice (provided from Asan Institute for Life Sciences Animal Lab., Seoul, Korea) were housed in specific pathogen free unit.

B16F10 cells ($2 \times 10^4$) suspended in 100 μl of RPMI 1640 serum-free medium were intravenously injected via tail vein. One week before tumor cell injection, the following 3 groups were treated.
1) RPMI control group
2) Dendritic cells (DC) ($5 \times 10^5$ cells/day)+tumor lysate treated group
3) Compound 3 (50 mg/kg/day) treated group.

In the case of DC+tumor lysate treated group, one week before melanoma injection, $5 \times 10^5$ DC cells mixed with tumor lysate were injected to the abdominal cavity every 1 weeks. In the case of Compound 3 treated group, 50 mg/kg/day of Compound 3 was treated to each mouse. One week before melanoma (B16F10) injection, Compound 3 (50 mg/kg/day) via P.O was continued 2 weeks on and 1 week off for 6 weeks. As a result, gross findings at $4^{th}$ week control group observed multiple metastatic lesions in both lungs. Compound 3 treated group and DC+tumor lysate treated group showed no evidence of disease in the lung (FIGS. 13, 14) and showed 90% survival rate in the observation for 6 weeks after melanoma (B16F10) injection (FIG. 15).

Based on the presumption that the anti-cancer effects of the Compound 3 are attributed to the activation of T-cells by Compound 3, cytotoxicity of T-cells activated by Compound 3 to malignant melanoma cells was investigated. As a result, when the ratio of T-cells activated by Compound 3 to melanoma cells was 100:1, cytotoxicity was 42% increased (FIG. 16).

EXPERIMENTAL EXAMPLE 6

Toxicity Test of Compound 3

Synthesized Compound 3 was dissolved in 5% ethanol solution which was orally administered at the 0.1 ml/20 g dose. Control group was treated 5% ethanol solution. IRC mice, housed in SPF facility were used as test animals. The animals were fasted for one day before drug administration, and had free access to water and chow thereafter. Eight to ten ICR mice, 25-35 g of weight, were grouped. The test agent was orally administered once at increasing doses ranging from 62.5 mg/kg, 125 mg/kg, 250 mg/kg, 500 mg/kg, 1.0 g/kg, to 2.0 g/kg. From the day of administration, survival number and any abnormal signs were observed with the naked eye for 14 days. $LD_{50}$ was calculated by the method of Lichfield-Wilcoxon (白須, 泰彦, 吐山, 豊秋:新毒性 試驗法 方法 と 評價—acute toxicity test, Realize Inc., Tokyo, 1988), and weight changes were calculated by the following Mathematical Formula.

Weight increment rate(%)={Weight of day 14−Weight of day 0}÷{Weight of day 0}×100    [Mathematical Formula 2]

The results are shown in Table 4. No toxicity was seen with 62.5 mg/kg~2 g/kg of Compound 3. This observation indicated that $LD_{50}$ was over 2 g/kg. Any abnormal sign as not observed with the naked eyes for 14 days after the administration. The weight of animals in treated group increased steadily so did in control animals. As shown in Table 5, no significant, treatment-specific weight change (gaining or losing) was observed.

TABLE 4

Death rate by the treatment o Compound 3 (%)

| | Dosage of Compound 3 (mg/kg) | | | | | | |
|---|---|---|---|---|---|---|---|
| | 0 | 62.5 | 125 | 250 | 500 | 1000 | 2000 |
| Number of dead mice/Number of orally administered mice | 0/10 | 1/8 | 0/8 | 1/8 | 2/9 | 0/9 | 0/9 |
| $LD_{50}$ | 0 | 12.5 | 30 | 12.5 | 22.2 | 0 | 0 |

TABLE 5

Weight increase 14 days after the oral-administration of Compound 3

| | Dosage of Compound 3 (mg/kg) | | | | | | |
|---|---|---|---|---|---|---|---|
| | 0 | 63 | 125 | 250 | 500 | 1000 | 2000 |
| Weight 14 days after Administration (g) | 38.7 ± 1.1 | 34.3 ± 0.1 | 38.1 ± 1.3 | 35.6 ± 1.4 | 36.5 ± 1.9 | 35.5 ± 1.1 | 35.9 ± 2.7 |
| Weight increment rate (%) | 16.9 | 11.9 | 17.3 | 11.2 | 10.1 | 9.5 | 14.4 |

Long term hepatotoxicity test was done on rats with Compound 3 dose at 100 mg/Kg body weight/day given P.O. for 4 weeks, and liver function test, lipid profile, cytochrome C-450 activity were observed. At the end of 4 weeks liver histology was observed. No significantly adverse effect was observed.

EXPERIMENTAL EXAMPLE 7

CLP (Cecal Ligation and Puncture) Test

CLP test was performed in order to confirm the effect of Compound 3 for prevention and treatment against septic shock. Ten 7-10 week old male inbred C3H/HeN mice (20-25 g of weight) were grouped. After 50 mg/kg/day of Compound 3 was orally administered to mice for 2 weeks on and 1 week off, mice were anesthetized with 80 mg/kg of ketamine and 16 mg/kg of rompun. Septic shock was induced by CLP model in anesthetized mice. One hour after inducing septic shock, 50 mg/kg of Compound 3 was treated, and then, the same treatment was continued for 3 days every 24 hours. Control group was orally administered PBS+5% ethanol solution. Survival rate of Compound 3 treated group and control group with time lapse was shown in Table 6. Compound 3 treated groups had 100% survival rate even after lapse of 120 hours.

TABLE 6

Survival rate in septic shock

| | Survival rate with time lapse | | | | | |
|---|---|---|---|---|---|---|
| | 0 hour Survival rate | 24 hours Survival rate | 48 hours Survival rate | 72 hours Survival rate | 96 hours Survival rate | 120 hours Survival rate |
| PBS treated group (control) | 100% | 60% | 40% | 40% | 40% | 40% |
| Compound 3 (50 mg/kg) | 100% | 100% | 100% | 100% | 100% | 100% |

MANUFACTURING EXAMPLE 1

Preparation of Medical Supplies Containing Compound 3 as an Effective Ingredient After confirming through the above experiments that Compound 3 had an excellent immunomodulating and anti-cancer activity, the present inventors prepared a treatment containing Compound 3 as an effective ingredient. Further, the followed manufacturing example of the treatment containing Compound 3 as an effective ingredient can be applied not only to the preparing of treatment but also to the preparing of health food. If there isn't extra mention, the symbol of % means weight % in the following manufacturing example.

MANUFACTURING EXAMPLE 1-1

Preparation of Soft Gelatin Capsules

MANUFACTURING EXAMPLE 1-1-1

| | |
|---|---|
| Compound 3 | 30% |
| Vitamin C | 4.5% |
| Vitamin D3 | 0.001% |
| Manganese sulfate | 0.1% |
| Wax | 10% |
| Palm oil | 25% |
| Safflower oil (Carthamus tinctorius) | 30.399% |

MANUFACTURING EXAMPLE 1-1-2

| | |
|---|---|
| Compound 3 | 31.25% |
| Evening primrose seed oil | 59.75% |
| Soy oil | 6.7% |
| Vitamin E acetate ester (DL-α-tocopherol acetate) | 2.1% |
| Soy lecithin | 0.2% |

MANUFACTURING EXAMPLE 1-1-3

| | |
|---|---|
| Compound 3 | 98.0% |
| Vitamin E acetate ester (DL-α-tocopherol acetate) | 2.0% |

MANUFACTURING EXAMPLE 1-2

Preparation of Tablets

| | |
|---|---|
| Compound 3 | 30% |
| Vitamin C | 10% |
| Vitamin D3 | 0.001% |
| Manganese sulfate | 0.1% |
| Crystalline cellulose | 25.0% |
| Lactose | 32.999% |
| Magnesium Stearate | 2% |

MANUFACTURING EXAMPLE 1-3

Preparing of an Injection Formulation

| | |
|---|---|
| Compound 3 | 2% |
| Propylene glycol | 35% |
| Mono glyceride | 8% |
| Ethanol | 5% |
| Water | 50% |

The injection formulation was prepared by the conventional method with above mentioned compositions and contents.

MANUFACTURING EXAMPLE 2

Preparation of Medical Supplies Containing Compound 1, 2, 4, and 5 as an Effective Ingredient Soft gelatin capsules, tablets and injection suspension were prepared by the same method and composition as described in the above manufacturing example 1, except the Compound 3 was substituted with Compound 1, 2, 4, and 5 at the same ratio.

MANUFACTURING EXAMPLE 3

Preparation of Health Food Containing Compound 3 as an Effective Ingredient

After confirming through the above examples that the Compound 3 had an excellent immunomodulating, anti-septic shock, and anti-cancer activity, the present inventors prepared health food containing the same as an effective ingredient.

MANUFACTURING EXAMPLE 3-1

Preparation of Beverages

| | |
|---|---|
| Honey | 522 mg |
| Thioctic amide | 5 mg |
| Nicotinic amide | 10 mg |
| Sodium riboflavin hydrochloride | 3 mg |
| pyridoxine hydrochloride | 2 mg |
| Inositol | 30 mg |
| Ortho acid | 50 mg |
| Compound 3 | 0.48~1.28 mg |
| water | 200 ml |

Beverage was prepared based on the above compositions and contents by following a conventional method.

MANUFACTURING EXAMPLE 3-2

Preparation of Chewing Gum

| | |
|---|---|
| Gum base | 20% |
| Sugar | 76.36~76.76% |
| Compound 3 | 0.24~0.64% |
| Fruit flavor | 1% |
| Water | 2% |

Chewing gum was prepared based on the above compositions and contents by following a conventional method.

MANUFACTURING EXAMPLE 3-3

Preparation of Candy

| | |
|---|---|
| Sugar | 50~60% |
| Starch syrup | 39.26~49.66% |
| Compound 3 | 0.24~0.64% |
| Orange flavor | 0.1% |

Candy was prepared based on the above compositions and contents by following a conventional method.

MANUFACTURING EXAMPLE 3-4

Preparation of Biscuit

| | |
|---|---|
| Strong flour $1^{st}$ class | 88 kg |
| Cake flour $1^{st}$ class | 76.4 kg |
| Refined sugar | 16.5 kg |
| Salt | 2.5 kg |
| Glucose | 2.7 kg |
| Palm shortening | 40.5 kg |
| Ammo | 5.3 kg |
| Baking soda | 0.6 kg |
| Sodium bisulfate | 0.55 kg |
| Rice flour | 5.0 kg |
| Vitamin B1 | 0.003 kg |
| Vitamin B2 | 0.003 kg |
| Milk flavor | 0.16 kg |
| Water | 71.1 kg |
| Whole milk powder | 4 kg |
| Substitute milk powder | 1 kg |
| Calcium phosphate, monobasic | 0.1 kg |
| Spraying salt | 1 kg |
| Spraying milk | 25 kg |
| Compound 3 | 0.2~0.5 kg |

Biscuit was prepared based on the above compositions and contents by following a conventional method.

MANUFACTURING EXAMPLE 3-5

Preparation of Ice Cream

| | |
|---|---|
| Milk fat | 10.0% |
| Milk solids non-fat | 10.8% |
| Sugar | 12.0% |
| Starch syrup | 3.0% |
| Emulsifying stabilizer (span) | 0.5% |
| Flavor (Strawberry) | 0.15% |
| Water | 63.31~62.91% |
| Compound 3 | 0.24~0.64% |

Ice cream was prepared based on the above compositions and contents by following a conventional method.

MANUFACTURING EXAMPLE 3-6

Preparation of Chocolate

| | |
|---|---|
| Sugar | 34.36~34.76% |
| Cocoa butter | 34% |
| Cocoa mat | 15% |
| Cocoa powder | 15% |
| Lecithin | 0.5% |
| Vanilla flavor | 0.5% |
| Compound 3 | 0.24~0.64% |

Chocolate was prepared based on the above compositions and contents by following a conventional method.

MANUFACTURING EXAMPLE 4

Preparation of Health Food Containing Compound 1, 2, 4, and 5 as an Effective Ingredient Beverage, chewing gum, candy, biscuit, ice cream and chocolate were prepared by the same method and composition as described in the above manufacturing example 3, except the Compound 3 was substituted with Compound 1, 2, 4, and 5 at the same ratio.

ADVANTAGEOUS EFFECTS

As explained hereinbefore, the mono acetyl diacyl glycerol derivatives containing Compound 3 shows significant effect for immuno modulation including immune enhancing. In the case of inducing cancer in a hamster by injecting cancer cell line, cancer development was delayed by activating lymphocytes, monocytes, and dendritic cells that are important factors to promote immunity and apoptosis of cancer cell was induced by promoting cytotoxicity of immune cell against caner cell. Also in the case of mouse induced septic shock, it shows 100% survival rate even after lapse of 120 hours by control of immune function and suppression effect of apoptosis. Therefore, mono acetyl diacyl glycerol derivatives according to the present invention can be effectively used for an immunomodulating agent, a sepsis treatment, a cancer treatment, and a health food for an immune modulation or the prevention of cancer.

The invention claimed is:

1. A method of treating sepsis comprising administering to a mammal an effective amount of mono acetyl diacyl glycerol defined by formula II in an isolated form:

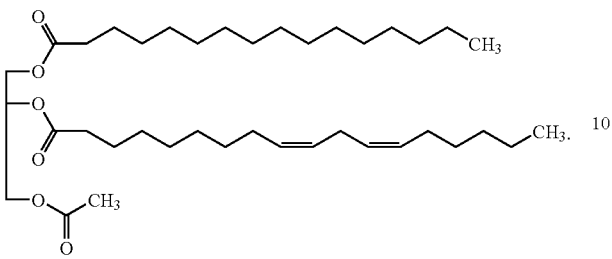
(II)

2. The method according to claim 1, wherein the mono acetyl diacyl glycerol derivative is administered in a pharmaceutical composition in an amount of 20 to 100 wt %.

3. The method according to claim 1, wherein the mono acetyl diacyl glycerol derivative is administered in health food.

* * * * *

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: ICAM-1 forward primer

<400> SEQUENCE: 1
```

-continued ccaactggaa gctgtttgag ct                                22

<210> SEQ ID NO 2
<211> LENGTH: 21
<212> TYPE: DNA
<213> ORGANISM: Artificial Sequence
<220> FEATURE:
<223> OTHER INFORMATION: ICAM-1 reverse primer

<400> SEQUENCE: 2
ttctgtcgaa ctccacagtc a                                 21

<210> SEQ ID NO 3
<211> LENGTH: 21
<212> TYPE: DNA
<213> ORGANISM: Artificial Sequence
<220> FEATURE:
<223> OTHER INFORMATION: ICAM-1 forward primer

<400> SEQUENCE: 3
catatggtcc gagaagcaga t                                 21

<210> SEQ ID NO 4
<211> LENGTH: 21
<212> TYPE: DNA
<213> ORGANISM: Artificial Sequence
<220> FEATURE:
<223> OTHER INFORMATION: ICAM-2 reverse primer

<400> SEQUENCE: 4
aagcatagca ggacagatgt c                                 21

<210> SEQ ID NO 5
<211> LENGTH: 24
<212> TYPE: DNA
<213> ORGANISM: Artificial Sequence
<220> FEATURE:
<223> OTHER INFORMATION: VCAM-1 forward primer

<400> SEQUENCE: 5
ggttgggaag ccggtcacag tcaa                              24

<210> SEQ ID NO 6
<211> LENGTH: 24
<212> TYPE: DNA
<213> ORGANISM: Artificial Sequence
<220> FEATURE:
<223> OTHER INFORMATION: VCAM-1 reverse primer

<400> SEQUENCE: 6
gcacacgtca gaacaaccga atcc                              24

<210> SEQ ID NO 7
<211> LENGTH: 24
<212> TYPE: DNA
<213> ORGANISM: Artificial Sequence
<220> FEATURE:
<223> OTHER INFORMATION: VLA-4 forward primer

<400> SEQUENCE: 7
ctcagatctc cttgttggag cagc                              24

<210> SEQ ID NO 8
<211> LENGTH: 21
<212> TYPE: DNA
<213> ORGANISM: Artificial Sequence

```
<220> FEATURE:
<223> OTHER INFORMATION: VLA-4 reverse primer

<400> SEQUENCE: 8
tgaatgcctg gtgtgtccta c                                              21

<210> SEQ ID NO 9
<211> LENGTH: 21
<212> TYPE: DNA
<213> ORGANISM: Artificial Sequence
<220> FEATURE:
<223> OTHER INFORMATION: VLA-5 forward primer

<400> SEQUENCE: 9
cagtggtgat gacactgatg a                                              21

<210> SEQ ID NO 10
<211> LENGTH: 21
<212> TYPE: DNA
<213> ORGANISM: Artificial Sequence
<220> FEATURE:
<223> OTHER INFORMATION: VLA-5 reverse primer

<400> SEQUENCE: 10
agaagctaag gttgatgcag g                                              21

<210> SEQ ID NO 11
<211> LENGTH: 20
<212> TYPE: DNA
<213> ORGANISM: Artificial Sequence
<220> FEATURE:
<223> OTHER INFORMATION: LFA-1 forward primer

<400> SEQUENCE: 11
tgacacttta cttgcgacca                                                20

<210> SEQ ID NO 12
<211> LENGTH: 21
<212> TYPE: DNA
<213> ORGANISM: Artificial Sequence
<220> FEATURE:
<223> OTHER INFORMATION: LFA-1 reverse primer

<400> SEQUENCE: 12
gatgggtagt cgaactcatt g                                              21

<210> SEQ ID NO 13
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 13
accacagtcc atgccatcac                                                20

<210> SEQ ID NO 14
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 14
tccaccaccc tgttgctgta                                                20
```